United States Patent [19]

Buscemi et al.

[11] Patent Number: 5,769,883
[45] Date of Patent: Jun. 23, 1998

[54] BIODEGRADABLE DRUG DELIVERY VASCULAR STENT

[75] Inventors: Paul J. Buscemi, Long Lake; Elizabeth A. Stejskal, St. Paul; Donald F. Palme, II, Dayton; Lixiao Wang, St. Paul, all of Minn.

[73] Assignee: SciMed Life Systems, Inc., Maple Grove, Minn.

[21] Appl. No.: 561,374

[22] Filed: Nov. 21, 1995

Related U.S. Application Data

[60] Division of Ser. No. 372,822, Jan. 13, 1995, Pat. No. 5,500,013, which is a continuation-in-part of Ser. No. 042,412, Apr. 2, 1993, abandoned, which is a continuation-in-part of Ser. No. 944,069, Sep. 11, 1992, abandoned, which is a continuation-in-part of Ser. No. 771,655, Oct. 4, 1991, abandoned.

[51] Int. Cl.⁶ .................................. A61F 2/06; A61F 2/04
[52] U.S. Cl. .................................. 623/1; 623/12; 606/195
[58] Field of Search .................................. 623/1, 11, 12; 600/36; 606/194, 195, 198

[56] References Cited

U.S. PATENT DOCUMENTS

| | | | |
|---|---|---|---|
| 4,167,045 | 9/1979 | Sawyer | 623/1 |
| 4,229,838 | 10/1980 | Mano | 623/1 |
| 4,749,585 | 6/1988 | Greco et al. | 623/1 |
| 4,787,900 | 11/1988 | Yannas | 623/1 |
| 4,801,299 | 1/1989 | Brendel | 623/1 |
| 4,814,120 | 3/1989 | Huc et al. | 623/1 |
| 4,822,361 | 4/1989 | Okita et al. | 623/12 |
| 4,950,258 | 8/1990 | Kawai et al. . | |
| 5,024,671 | 6/1991 | Tu et al. . | |
| 5,028,597 | 7/1991 | Kodama et al. | 623/11 |
| 5,092,885 | 3/1992 | Yamada et al. . | |
| 5,100,429 | 3/1992 | Sinofsky et al. . | |
| 5,147,370 | 9/1992 | McNamara et al. . | |
| 5,201,778 | 4/1993 | Brotzu et al. . | |
| 5,234,457 | 8/1993 | Andersen . | |
| 5,376,376 | 12/1994 | Li . | |
| 5,575,815 | 11/1996 | Slepian et al. | 623/1 |

FOREIGN PATENT DOCUMENTS

| | | |
|---|---|---|
| 0 211 570 | 2/1987 | European Pat. Off. . |
| 0 420 541 A2 | 4/1991 | European Pat. Off. . |
| WO 87/04935 | 8/1987 | WIPO . |
| WO 93/06792 | 4/1993 | WIPO . |

OTHER PUBLICATIONS

"Biosynthesis of Heparin and Heparan Sulfate", Ulf Lindahl and Lena Kjellen, Biology of Proteoglycans, 1987.
"Molecular Biology of Proteoglycans and Link Proteins", Linda J. Sandell, Biology of Proteoglycans, 1987.
"Blood, Coagulants and Anticoagulants", Encyclopedia of Chemical Technology, vol. 4, Third Edition.

*Primary Examiner*—Debra S. Brittingham
*Attorney, Agent, or Firm*—Vidas, Arrett & Steinkraus, P.A.

[57] ABSTRACT

A stent includes a main body of a generally tubular shape for insertion into a lumen of a vessel of a living being. The tubular main body includes a substantially biodegradable matrix having collagen IV and laminin that enclose voids within the matrix. The tubular main body also includes a biodegradable strengthening material in contact with the matrix to strengthen the matrix. The tubular main body is essentially saturated with drugs.

6 Claims, 3 Drawing Sheets

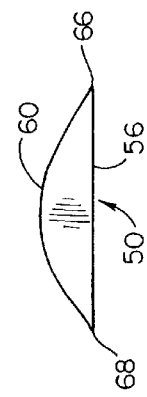
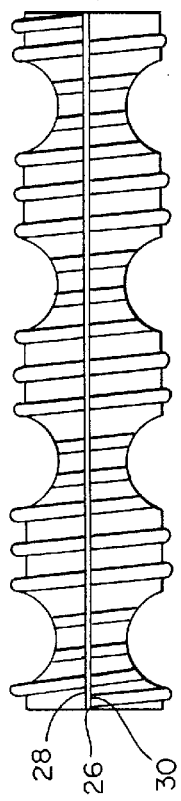
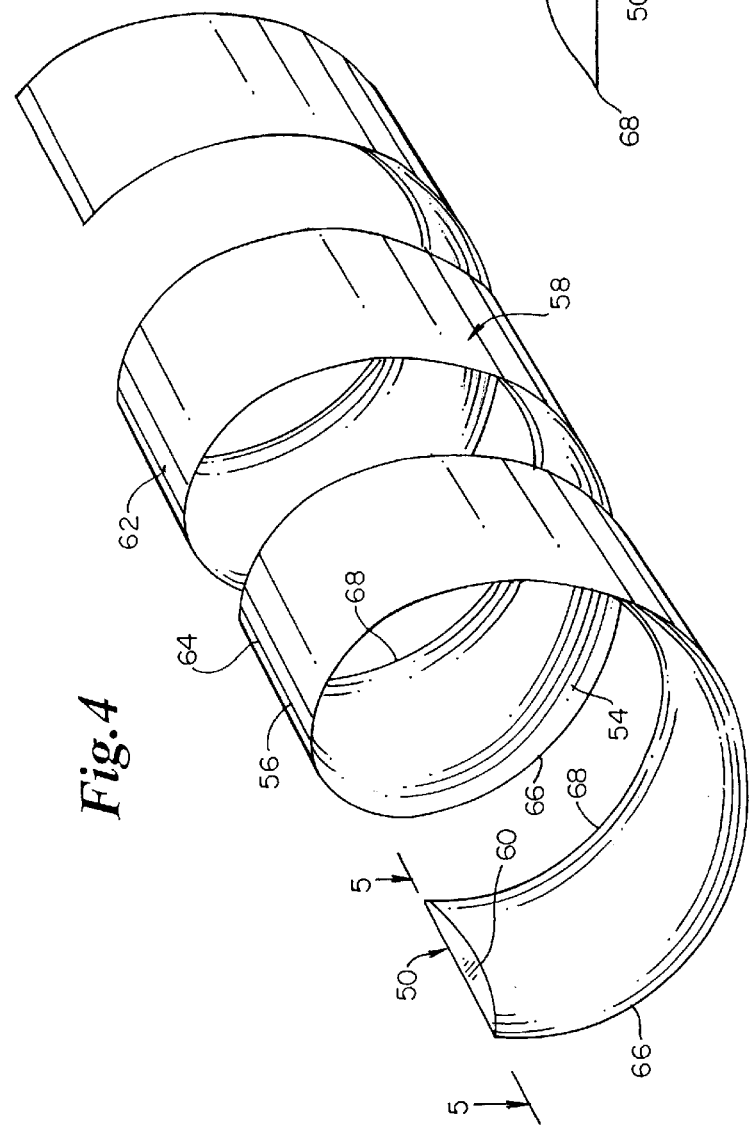

BIODEGRADABLE DRUG DELIVERY VASCULAR STENT

This application is an Divisional application from Ser. No. 08/372,822 filed Jan. 13, 1995, now U.S. Pat. No. 5,500,813, which was a Continuation-In-Part of Ser. No. 08/042,412 filed Apr. 2, 1993, now abandoned, which was a Continuation-In-Part of Ser. No. 07/944,069 filed Sep. 11, 1992, now abandoned, which was a Continuation-In-Part of Ser. No. 07/771,655 filed Oct. 4, 1991, now abandoned.

BACKGROUND OF THE INVENTION

This invention relates to a device for providing mechanical support and a uniform release of drugs to a vessel lumen of a living being.

A variety of medical situations requires the use of a mechanism to expand and support a constricted vessel and to maintain an open passageway through the vessel. A few examples of such situations following angioplasty include holding a dissection in place, preventing closure during spasm, and preventing acute closure due to thrombosis. In these situations, devices, commonly known as stents, are useful to prevent stenosis of a dilated vessel, or to eliminate the danger of occlusion caused by "flaps" resulting from intimal tears that may be associated with angioplasty, or to hold two ends of a vessel in place.

Stents have been made using materials of varied composition and conformation. McGreevy et al. U.S. Pat. Nos. 4,690,684 and 4,770,176, describe a meltable stent that is inserted into the interior of the ends of a blood vessel during anastomosis. Anastomosis refers to the surgical or physical connection of two tubular structures, such as veins or arteries. The stent is made of blood plasma, which is biologically compatible with the living being and which melts rapidly in response to heat.

The Fischell et al. U.S. Pat. No. 4,768,5107, describes an intravascular stent which is an unrestrained coil spring having an outside diameter of 2 to 12 millimeters and a length of 5 to 25 millimeters. The materials of construction are stainless steel, and a titanium alloy. Decreased thrombogenicity is achievable by coating the outside of the coil with a non-thrombogenic material such as ULTI carbon.

The Leeven et al. U.S. Pat. No. 4,820,298, describes a stent having a flexible tubular body made from a thermal plastic to the form of a helix. Polyester and polycarbonate copolymers are selected as particularly desirable materials.

The Wolff et al. U.S. Pat. No. 4,830,003, describes a stent made from wires formed into a cylinder. The wires are made of a biocompatible metal. Biocompatible metals include 300 series stainless steels such as 316 LSS, as well as platinum and platinum-iridium alloys, cobalt-chromium alloys such as MP35N, and unalloyed titanium.

The Wiktor U.S. Pat. No. 4,886,062, describes a stent made from low memory metal such as a copper alloy, titanium, or gold. The stent is preformed into a two-dimensional zig-zag form creating a flat expandable band.

The Gianturco U.S. Pat. No. 4,907,336, describes a wire stent having a cylindrical shape that results from an expandable serpentine configuration. Malleable materials of construction are preferably included from the group of annealed stainless steels, tungsten and platinum.

Goldberg et al., Canadian Application 2,025,626, describe a bio-degradable infusion stent used to treat ureteral obstructions. The application describes an extruded material of construction made of epsilon-caprolactone (15–25% w/w of terpolymer composition); glycoside (5–50% w/w) and L(–) lactide (45–85% w/w). This material was described as having a minimum tensile strength of at least 500 pounds per square inch, preferably 650 psi; elongation of greater than 10%, preferably greater than 100%; and Shore A hardness equal to 50–100%, preferably 75–95%. The Goldberg et al. patent application describes a method for incorporating radiopaque materials such as barium sulfate into the polymer in amounts ranging from 5–30%. The mechanism of biodegradation is described as hydrolysis resulting in degradable products excreted in urine or reabsorbed into tissues. The duration of functional life of the stent is estimated at about 3–7 weeks.

The Wilcoff U.S. Pat. No. 4,990,155, describes a plastic stent having an inherently expandable coil conformation. The "inherency" results from an elastic memory conferred by electron beam radiation imparting cross-linkages that provide an inherent tendency to return to a given diameter after any distortion. Materials of construction include high density polyethylene. Optionally, this material is compounded with an anti-coagulant and/or an x-ray opaque material such as bismuth-sub-carbonate.

The Shockley et al. U.S. Pat. No. 4,994,033, describes a drug delivery dilatation catheter having three flexible, plastic tubes concentrically arranged relative to each other. The outermost sleeve of this catheter contains microholes for drug delivery. These microholes are made with a laser beam. Drugs that can be delivered by this system include aspirin, persantin, heparin, and prostaglandins. Drugs are delivered when externally applied pressure causes the innermost sleeve to balloon out. The drug is then forced through the microholes to spray and to treat a lesion.

Sigwart, Canadian Patent Application 2,008,312, describes a stent made from a malleable flat sheet having a reticulated pattern. The reticulated pattern includes non-deformable squares or diamonds. The stent is made by rolling the sheet and locking the sheet into a spiral having a small diameter. The sheet is locked into a spiral by a tie interwoven into the reticulated pattern. Once inserted into the lumen of a vessel, the spiral is expanded and held in place by flaps integrated into the outer body of the stent.

The Kawai et al. U.S. Pat. No. 4,950,258, describes a biodegradable molded product having a first shape. The molded product is deformed at an elevated deforming temperature to form a second shape. The product is then cooled. When the product is reheated to a prescribed temperature, the product recovers the first shape.

The Brandley et al. U.S. Pat. No. 5,032,679, describes a glycosaminoglycoside (GAG) composition made of tetrasaccharide units derived from heparin/heparin sulfate. The composition has use in preventing proliferation of smooth muscle cells.

The Mares et al. U.S. Pat. No. 5,061,281, describes a medical device made from a resorbable homopolymer derived from the polymerization of an alphahydroxy carboxylic acid. The resorbable homopolymer has an average molecular weight of from 234,000 to 320,000 as measured by gel permeation chromatography.

The Sinclair U.S. Pat. No. 4,057,537, describes a copolymer prepared by copolymerizing an optically active lactide and epsilon caprolactone in the presence of a tin ester of carboxylic acid. The copolymer is biodegradable.

The Seilor, Jr. et al. U.S. Pat. No. 4,550,447, describes a porous tube for use in a lumen of a vessel. The porous tube includes ribs for ingrowth. Pores of the porous tube promote tissue ingrowth.

The Spears U.S. Pat. No. 4,799,479, describes the use of a heated balloon to fuse tissue of a blood vessel. The balloon is heated by a laser.

The Spears U.S. Pat. No. 5,092,841, describes the use of a heated balloon to bond a bioprotective material to an arterial wall. The bioprotective material permeates into fissures and vessels of the arterial wall.

The Sawyer U.S. Pat. No. 5,108,417, describes a stent made from a helically shaped titanium or aluminum strip having an airfoil on an interior surface. The airfoil increases blood flow velocity through the stent.

The Hillstead U.S. Pat. No. 5,116,318, describes a dilation balloon assembly that includes an expandable sleeve. The expandable sleeve, positioned around a balloon of the assembly, eliminates a formation of "blade-like" edges on the balloon.

The Savin et al. U.S. Pat. No. 4,950,227, describes a stent delivery system that includes a pair of expandable cuffs that are positioned over opposing ends of a stent. The stent is positioned around a balloon attached to a catheter. The cuffs are positioned around the catheter so that when the balloon expands, expanding the stent, the stent is released from the cuffs.

Cox et al. in *Coron. Artery Dis.* 3 at 3 (1992) describe a tantalum stent that is balloon expandable and is coated with a cellulose ester. The cellulose ester includes methotrexate, heparin or a combination of both drugs.

The stents mentioned do not remedy all problems relating to stents. In particular, some uses require stents to safely degrade within the bloodstream of an artery or vein over a period of weeks to months. Such stents must meet particular criteria. For instance, such stents must be compatible with surrounding tissue in the vein or artery as well as with blood flowing through the vein or artery. Degradation products must be prevented from forming emboli.

Stents should also optimize flow through a vein or artery. Additionally, there is a need for stents which deliver agents or drugs to blood passing through the vein or artery that are generally beneficial to the recipient. Also desired are stents which can deliver drugs or biologically active agents at a controlled rate to blood passing through the vessel lumen as well as to the vessel wall.

SUMMARY OF THE INVENTION

The present invention includes a biodegradable stent having a tubular main body made of a matrix, essentially saturated with drugs, that includes collagen IV and laminin. The matrix is strengthened with a strengthening biodegradable material such as polylactic acid.

BRIEF DESCRIPTION OF THE DRAWINGS

FIG. 3 is an overview of one embodiment of opposing edges bounding a slot extending lengthwise along the main body of the stent of the present invention.

FIG. 4 is an enlarged perspective view of a coiled stent embodiment of the present invention.

FIG. 5 is a cross-sectional view of a main body of the coiled stent embodiment of the present invention.

DETAILED DESCRIPTION OF THE PREFERRED EMBODIMENTS

Figure 1:
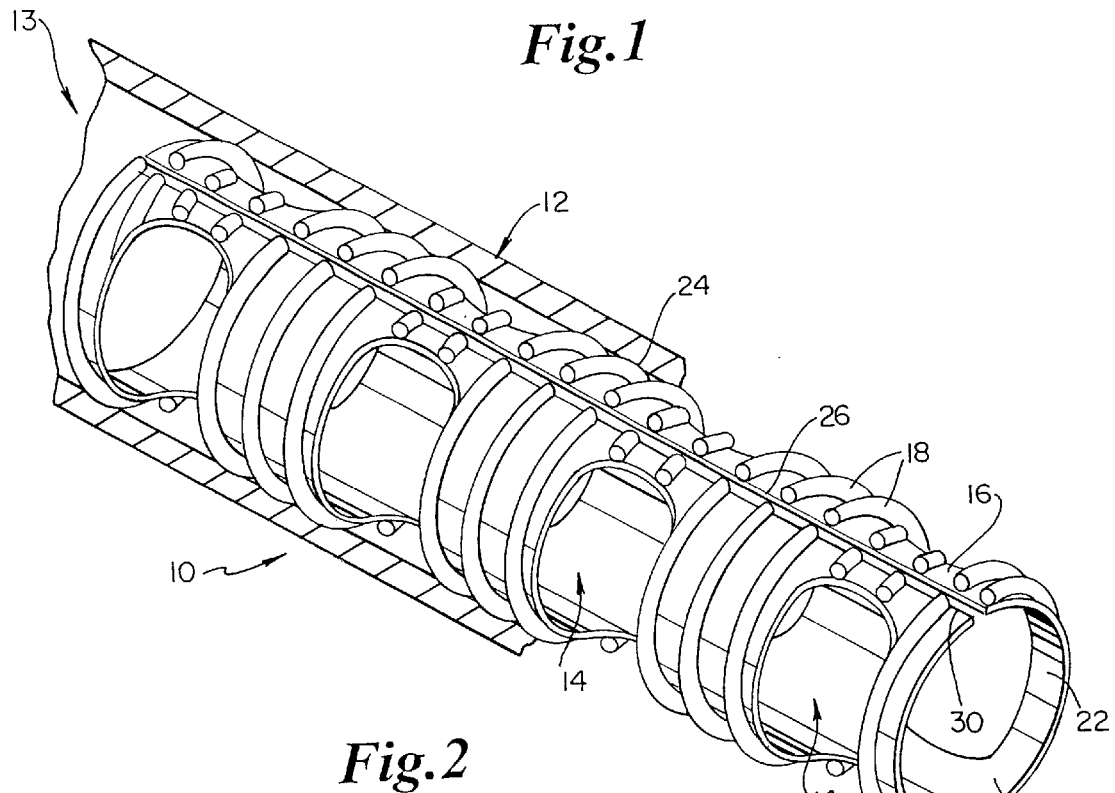
FIG. 1 is an enlarged perspective view of one embodiment of the stent of the present invention.

The present invention includes a biodegradable stent generally illustrated at 10 in FIG. 1. The stent 10 releases drugs into a tubular vessel 12 having a lumen 13 in a living being. The rate of drug release is controlled by the rate of degradation of the biodegradable materials. The stent 10 also provides mechanical support to a tubular vessel 12 in a living being. The stent strengthens an area of the vessel that is in contact with the stent 10.

The stent 10 includes a generally tubular main body 11 and a plurality of fibers 18 disposed around the main body 11. A plurality of apertures 14 extend through the stent 10. The stent 10 also includes a slot 26 extending the length of the stent.

Figure 2:
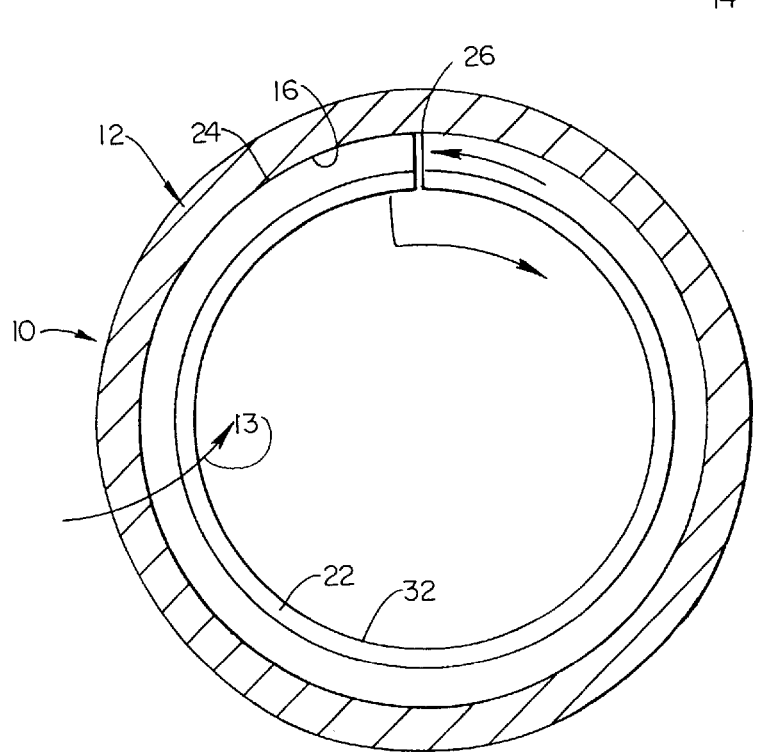
FIG. 2 is a cross-sectional view of the stent.

The tubular main body 11 includes an outer surface 16 and inner surface 22. The outer surface 116 of the main body 11 faces an inner surface wall 24 of the vessel 12. The inner surface 22 of the stent 10 faces a stream flowing through the lumen 13 as shown in cross section in FIG. 2. The stent of the present invention may range from 1 millimeter in diameter to 50 millimeters in diameter and from 1 millimeter in length to 50 millimeters in length. The size of the stent is dictated by the lumen of the vessel to which the stent is placed. The tubular main body suitably has a length of up to approximately 5 centimeters.

The plurality of fibers 18 disposed around the main body 11 contacts the outer surface 16 of the main body. In one preferred embodiment, the fibers are arranged concentrically around the main body, encircling the outer surface 16 in an annular alignment. The annular alignment is ordered so that individual fibers are separated by approximately the same distance. Alternatively, the fibers are arranged in annular pairs or triplets. In another embodiment, the plurality of fibers abut each other in annular alignment.

In another embodiment, the plurality of fibers 18 of the outer surface are braided. Braided fibers are also arranged in annular alignment around the main body of the stent 10. In one other embodiment, the fibers are woven. Woven fibers increase the stretch and flexibility of the stent compared to fibers which are not woven. Solid fibers, hollow fibers, or a combination thereof can be used for any of the embodiments described above.

The plurality of fibers 18 of the main body 11 can be formed by techniques well known in the art. These techniques include melt, wet and dry spinning. High molecular weight polymers having a range of 200,000 to 3,000,000 daltons are preferred for successful fiber production. One example of a biodegradable material meeting this criterion for fiber manufacture is poly-L-lactide.

The fibers generally undergo further orientation in the extruded direction. One technique for orienting the fibers is to stretch the fibers at a temperature range of 50° to 150° C.

Desirably, the plurality of fibers 18 disposed around the main body 11 of the stent 10 have an outer diameter not exceeding approximately 0.2 millimeters; In the case of hollow fibers, the wall thicknesses should be within the approximate range of 25 to 100 microns. Preferably, the fibers should have a tensile strength in a range of 4,000 to 500,000 pounds per square inch and have a modulus of 200,000 to 2,000,000 pounds per square inch.

In one embodiment, the main body includes a film that is preferably combined with the plurality of fibers disposed around the main body 11. The film combined with the plurality of fibers defines the outer surface 16 of the main body. The plurality of fibers can be combined with the film using any number of conventional methods. In one conventional method, solvation sealing, the steps of heat pressing and extrusion molding combine the film and fiber production into one step for the orientation of the polymer materials. Additional methods include solvent sealing of the fibers to the film or heat melting processes for the annealing of the multiple layers. By the salvation sealing method, fibers and film are combined to form the outer surface into a single biodegradable material matrix.

Preferably, the main body 11 of the stent 10 includes a film 32, covering the inner surface 22. The film 32 of the inner surface 22 is formed bog conventional methods such as heat or pressure extrusion or solution casting.

Additionally, the present invention includes an embodiment where the inner surface 22 and the outer surface 16 of the main body 11 are separated by at least one interior film layer. The interior film layer is integrated into the main body by multiple casting with the inner and outer surfaces. The present invention further includes a main body having more than one biodegradable interior film layer. Desirably, the thickness of the main body does not exceed approximately 0.25 millimeters.

The plurality of apertures of the present invention is preferably ordered around the main body to form rows of apertures. FIG. 1 illustrates two rows of apertures, the length of each row extending the length of the tubular main body. In an alternative embodiment, the plurality of apertures are ordered to form one row having a length extending the length of the tubular main body. The apertures within the one row are bounded by edges 28 and 30 bordering the slot 26. In one other embodiment, the plurality of apertures are ordered to form a row extending less than the length of the main body of the stent. In another embodiment, the plurality of apertures are not ordered but are located randomly over the main body of the stent.

Suitable shapes for the individual apertures include both asymmetrical and symmetrical shapes such as ovals, circles, or rectangles. Also, apertures may be made in a variety of sizes. The apertures can be formed by any conventional means such as stamping.

The slot 26 extends the length of the stent and is defined by opposing edges 28 and 30 of the main body as illustrated in FIG. 3. In a preferred embodiment, the fibers 18 are oriented fibers and are fixed to the outer surface 16 of the main body 11. When the slot 26 is formed, the oriented fibers 18 provide a spring force in an outward substantially radial direction. The outward spring force increases the effective diameter of the main body while the slot permits compression or reduction of the effective diameter. Once formed, the stent is normally at its effective maximum diameter and the slot is at its widest.

In use, the stent is positioned at the inner surface wall 24 of the vessel 12 by radially compressing the stent to a tubular diameter less than the diameter of the vessel 12 and moving the stent to a desired site within the vessel. The stent is secured by releasing the stent from compression so that the stent can radially spring out to abut against the inner surface wall 22 of the vessel 12.

In the most preferred embodiment, the biodegradable stent of the present invention is made of biodegradable materials that are also biocompatible. By biodegradable is meant that a material will undergo breakdown or decomposition into harmless compounds as part of a normal biological process. It is important to the present invention that the plurality of apertures 14 in the main body 11 of the stent promote the successful biodegradation of the stent 10. Optimally, the plurality of apertures 14 permits epithelial cells to grow on the stent 10. It is believed that the epithelial cell growth will encapsulate particles of the stent during biodegradation that would otherwise come loose and form emboli in the bloodstream.

Suitable biodegradable materials for the main body 11 of the stent 10 of the present invention include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Biodegradable glass or bioactive glass is also a suitable biodegradable material for use in the present invention. Preferably the materials have been approved by the U.S. Food arid Drug Administration.

The present invention includes a biodegradable stent incorporating a variety of biodegradable materials within it. For instance, in one embodiment, the film and fibers covering the inner surface 22 of the main body 11 of the biodegradable stent is made of either polylactic acid, polyglycolic acid (PGA), collagen or other connective proteins or natural materials, polycaprolactone, copolymers of these materials as well as composites thereof and combinations of other biodegradable polymers. The film covering the outer surface 16 along with the plurality of fibers 18 are made of either collagen, hylauric acid, adhesive proteins, copolymers of these materials as well as composites and combinations thereof. The present invention includes an embodiment where fibers are made from more than one biodegradable material. Also, the present invention includes an embodiment where the film is made from a biodegradable material different from the fibers.

One other embodiment of the biodegradable stent of the present invention includes a biodegradable coiled stent, illustrated at 50 in FIG. 4. The coiled stent 50 includes a main body strip 58 made of a, biodegradable material, having an exterior surface 56, a cambered interior surface 54, a leading end 66 and a trailing end 68 opposing the leading end. The biodegradable coiled stent 50 is most preferably helically coiled.

The biodegradable coiled stent 50 most preferably has a length-to-diameter ratio of at least about 1-to-2. The length-to-diameter ratio of at least about 1-to-2 prevents the coiled stent from flipping out of position and tumbling through the lumen. In one embodiment, the coiled stent 50 has a length of at least about 3 mm. The main body strip 58 of the coiled stent 50 is preferably made from a strip of biodegradable material having a width of about 2 millimeters.

The main body strip 58 is most preferably formed into a plurality of individual, integral coils as shown at 62 and 64 to make the coiled stent 50. The individual, integral coils 62 and 64 are spaced to permit epithelial cells to grow on the coiled stent 50.

The exterior surface 56 of the main body strip 58 faces the lumen of the vessel. The exterior surface 56 is preferably textured by a plurality of pores (not shown). The plurality of pores are sized and positioned in order to promote adhesion of the coiled stent 50 to the vessel wall. Specifically, the pores are sized to promote ingrowth of cells of the vessel wall onto the exterior surface 56. In one embodiment, the pores have a diameter within a range of about 0.1 to 30.0 microns and an apparent density of about 10 to 70% of a non-porous material density.

The cambered interior surface 54 of the main body strip 58 contacts the fluid stream passing through the lumen of the vessel once the strip 58 has been coiled and inserted into the lumen. The cambered interior surface 54 is preferably symmetrical and smooth. The cambered interior surface 54 of the main body strip 58 includes a camber 60, most preferably having a maximum angle of curvature within a range of about 10 to 20 degrees. The camber 60 extends outwardly, into the fluid stream, in a convex fashion as shown in cross-section in FIG. 5.

The leading end 66 of the main body strip 58 faces a direction of flow of fluid passing through the vessel lumen. The trailing end 68 opposes the leading end 66. Most preferably, the main body strip 58 has a thickness that is substantially the same at the leading end 66 as at the trailing end 68. In one preferred thickness profile embodiment for the main body strip 58 illustrated in FIG. 5, the main body 58 has a minimum thickness at the leading end 66 and trailing end 68. Preferably, the thickness is symmetrically tapered to approach zero microns at each of the leading end 66 and trailing end 68.

The cambered interior surface 54, the leading end 66 and the trailing end 68 together prevent the formation of eddys, formed in a wake that is made when a fluid such as blood passes through each coil 62 and 64 of the coiled stent 50. The cambered interior surface 54, leading end 66 and trailing end 68 are also believed to reduce the wake size for each coil 62 and 64 and are believed to reduce pressure drag on each coil 62 and 64.

To install in a lumen of a vessel, the coiled stent 50 is positioned at a wall (not shown) of the lumen by radially compressing the stent to a tubular diameter less than the diameter of the vessel and moving the stent 50 to a desired site within the vessel. The stent 50 is secured by releasing the stent 50 from compression so that the stent 50 can radially spring out to abut against the wall of the vessel.

In one installation embodiment, the biodegradable coiled stent 50 includes a plurality of microcapsules that are dispersed in the biodegradable material. The microcapsules contain a material that induces crosslinking of the biodegradable material. The biodegradable stent including the plurality of microcapsules is further expanded while in the lumen and is heated with a heated balloon and is cooled while the stent is in an expanded position.

The balloon contacts the cambered interior surface 54 of the coiled stent 50 and heats the stent with a magnitude of thermal energy that will cause the microcapsules to burst and release the material that induces crosslinking. Crosslinking the biodegradable material imparts a strength to the stent sufficient to hold open the lumen.

The thermal energy will not be of a magnitude great enough to change surrounding lumen tissue. In particular, the thermal energy will not either fuse lumen tissue or cause a bonding of tissue with the stent. To the contrary, it is important to the coiled stent embodiment 50 of the present invention that thermal energy from the balloon not change living lumen tissue.

The thermal energy includes energy derived from heated fluids, electromagnetic energy and ultrasonic energy. In one embodiment, the thermal energy heats the biodegradable material of the stent to a temperature above a glass transition temperature of the biodegradable material but below a melting point of the material.

In one other embodiment, the thermal energy heats the biodegradable material of the stent to a first temperature that is lower than the glass transition temperature of the biodegradable material. Then, the stent is heated to a second temperature above the glass transition temperature of the biodegradable material.

Once the biodegradable material of the stent is heated above its glass transition temperature, the material softens. The balloon is then expanded. The expanded balloon radially enlarges the diameter of the stent. The stent, having an enlarged diameter, is then allowed to cool in an expanded position and the balloon is removed. In one other embodiment, the stent is expanded by the balloon before being heated to a temperature above the glass transition temperature of its biodegradable material.

The present invention includes one other installation embodiment for a biodegradable stent having a biodegradable tubular main body. The biodegradable tubular main body is made of a deformable, biodegradable material that overlays a balloon of a catheter. When the deformable, biodegradable material overlays the balloon, the material assumes a shape of the tubular main body. Acceptable tubular shapes include a slotted tubular shape as shown in FIG. 1 and a helically coiled shape as shown in FIG. 4. The deformable, biodegradable material is preferably coated with a biodegradable, biocompatable film that adheres the biodegradable material to the balloon.

In one embodiment, the biodegradable film forms a water soluble, viscous interface between the tubular main body and the balloon when wetted. The film gradually dissolves in a water component of blood while passing through the lumen. The biodegradable film dissolves at a rate that permits adherence of the tubular main body to the balloon by the film during passage of the stent and balloon through the lumen and during an expansion of the balloon and the tubular main body. However, the film is dissolved once the stent is expanded to a degree that permits the stent to be separated from the balloon. The water soluble film is acceptably made from materials that include high molecular weight polyethylene glycol, high molecular weight carbohydrates and high molecular weight polyvinylpyrrolidone. The water soluble film also acceptably includes an antithrombic drug to aid in the reduction of thrombosis.

In another embodiment, the biodegradable, biocompatable film is meltable upon application of thermal energy. The meltable film is acceptably made from ionic, crosslinked polymers that include combinations of anionic carbohydrates with polycations.

The balloon of the catheter, having the biodegradable tubular main body adhered, is positioned within the lumen at a site where the tubular main body of the stent is to be installed. Once positioned, the balloon is expanded, radially expanding the diameter of the tubular main body. The biodegradable tubular main body is then heated to a temperature above the glass transition temperature and below a melting temperature of the biodegradable material, softening the biodegradable material of the tubular main body. Heating the tubular main body also melts the meltable film coating of the tubular main body, permitting release of the tubular main body from the balloon.

The source of energy for heating the tubular main body is suitably derived from heated fluids, electromagnetic energy and ultrasonic energy. In one embodiment, a fluid contained in the balloon is heated by a heating element also contained in the balloon.

The tubular main body is subsequently allowed to cool. Once the main body is cooled, the balloon is deflated and removed from the lumen. The cooled and strengthened biodegradable stent remains in the lumen.

The present invention also includes embodiments where the deformable, biodegradable material of the tubular main body is strengthened by an application of mechanical energy. In one embodiment, the mechanical energy is applied to the tubular main body to reorient molecules of the biodegradable material of the stent. The mechanical energy is applied at a temperature below a glass transition temperature of the material. The mechanical energy is of a magnitude below an elastic limit of the biodegradable material.

In another embodiment using mechanical energy, the biodegradable material of the tubular main body includes the plurality of microcapsules. The microcapsules include materials that induce crosslinking in the biodegradable material. The mechanical energy is applied to the tubular main body in order to burst the microcapsules. Once burst, the microcapsules release the materials that induce crosslinking of the biodegradable material. The biodegradable material is then crosslinked and is strengthened.

The mechanical energy is applied by inflating the balloon to which the tubular main body is adhered. Inflating the balloon radially expands and stretches the deformable, biodegradable material of the tubular main body. The stretching is of a magnitude to reorient molecules of one stent embodiment. The stretching is also of a magnitude to burst microcapsules contained in the biodegradable material of the second embodiment.

In one embodiment of the biodegradable coiled stent 50, the main body 58 is made from a single individual biodegradable material such as polylactic acid (pla). Preferably, the pla has a low degree of polymerization (dp).

In one other embodiment, the main body 58 is made from a plurality of individual, biodegradable materials arranged in layers. Each of the individual, biodegradable layers has distinct physical and chemical properties.

In one layered embodiment of the coiled stent 50, an inner layer contacting the fluid passing through the vessel lumen, is made of either polylactic acid, polyglycolic acid (PGA), collagen or other connective proteins or natural materials, polycaprolactone, copolymers of these materials as well as composites thereof and combinations of other biodegradable polymers. An outer layer, contacting a wall of the vessel lumen, is made of either collagen, hylauric acid, adhesive proteins, copolymers of these materials as well as composites and combinations thereof.

Figure 6:
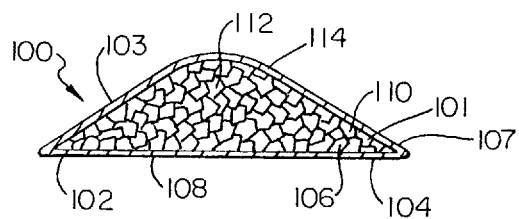
FIG. 6 is a cross-sectional view of one embodiment of a main body of the biodegradable coiled stent of the present invention.

One particular embodiment of the coiled stent, illustrated at 100 in FIG. 6, is made of a matrix 101 that includes collagen IV and laminin. In one embodiment, the matrix 101 also includes heparin.

The matrix 101 includes essentially quasi-crystalline regions 102 having interfaces 103 with collagen IV concentrated at the interfaces 103. The interfaces 103 of collagen IV enclose voids 105 within the matrix 101.

Figure 7:
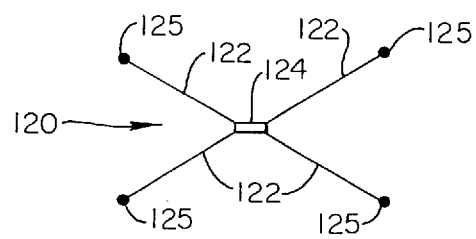
FIG. 7 is a schematic view of a collagen IV tetramer.

The type IV collagen component of the matrix 101 is a highly specialized form of collagen protein found primarily in basement membranes. The type IV collagen protein molecule has a tertiary structure unlike any other collagen type. It is believed that the tertiary structure of type IV collagen is a tetramer formed by four triple-helical collagen molecules, such as is illustrated at 120 in FIG. 7. The triple-helical collagen molecules form arms 122 of the tetramer 120. The arms 122 function as flexible spacers. Each triple-helical collagen molecule overlaps at an amino terminii to form a 7 S collagen fragment at a center 124 of the tetramer 120. The 7 S collagen fragment is a disulfide fragment that is resistant to collagenase enzyme. Also, a C-terminal globular domain (not shown) of the type IV collagen molecule is included as an integral part of the final collagen IV matrix 101.

The type IV collagen tetramers form the quasi-crystalline regions 102 within the matrix 101. The quasi-crystalline regions 102 have an irregular polygonal structure formed from the tetragonal tertiary structure of the collagen IV molecules.

Within the matrix 101, the collagen IV tetramers are connected to one another via their amino-termini 125. Flexibility of the quasi-crystalline regions of the matrix 101 is introduced by a frequent interruption of a particular amino acid sequence, (Gly-X-Y)n, within the triple helical arms 122 of the collagen IV tetramers 120. The amino acid sequence interruption disrupts the triple helical configuration of the arms 122.

The role of laminin as a component of the matrix 101 is believed to be one of aiding in the organizing of the collagen IV and heparin to form the matrix 101. Laminin is a glycoprotein having two or three short chains, each having a molecular weight of about 200,000 daltons and one long chain having a molecular weight of about 400,000 daltons. The chains are held together by disulfide bonds. Electron microscopy of rotary shadowed laminin has revealed that laminin has a cross-shaped structure with rodlike segments and globular domains.

Laminin binds the components of collagen IV and heparin to make the matrix 101. Specifically, laminin includes collagen IV binding sites on the short chains and a heparin binding site at a globular end of the long chain. In addition to binding collagen IV and heparin, laminin aids in organizing the matrix 101. Laninin also promotes an attachment of epithelial cells to type IV collagen-coated substrates.

The heparin component of the matrix 101 is a glycosaminoglucuronan (gag) having a molecular weight within a range of about 6000 to 25,000 molecular weight units. The heparin component binds with laminin to make the matrix 101 of the stent 100 of the present invention. The present invention acceptably includes moieties of the glycosaminoglycoside group in addition to heparin. The moieties include residues of D-glucuronic acid.

In one other embodiment, the stent 100 includes polylactic acid having crystalline regions. The matrix 101 made of collagen IV and laminin, when wet, has a strength that is not sufficient to hold open the lumen of the vessel of the living being. The polylactic acid imparts structural integrity to the stent 100.

In one embodiment, the polylactic acid is interspersed as particles within the matrix 101 (not shown) to strengthen the matrix 101. In one other embodiment, the polylactic acid is positioned on the outer surface 114 of the stent 100 as a layer 107.

In one preferred embodiment, the matrix 101 is essentially saturated with drugs. The drugs are included within the voids 105 within the quasi-crystalline membrane matrix 101, particularly if the drugs are hydrophilic. In one embodiment, the drugs are included within the polylactic acid polymer, particularly if the drugs are hydrophobic.

In one embodiment, the drugs are in a liquid phase and are mixed to form a liquid drug mixture. The drug mixture is used to substantially fill the voids 105 within the matrix 101.

In one other embodiment, the drugs are included within microcapsules. The microcapsules may be added to any of the voids 105, the polylactic acid 107 and the collagen/laminin/heparin matrix 101.

In one further embodiment, the drugs include both a liquid phase and a microcapsule phase. Both the liquid and the microcapsules are added to the voids 105.

Preferably, the matrix 101 includes drugs performing particular functions within particular portions of the coiled stent 100. For instance, the stent 100 includes an inner portion 104 having a surface 106 that interfaces with a vascular wall 108 of the lumen. This inner portion 104 and surface 106 are essentially saturated with drugs that are released as the matrix 101 degrades. The drugs that are released preferably include those promoting epithelial cell growth.

As the matrix 101 degrades, the inner portion 104 recedes. The inner surface 106 also recedes and releases drugs that promote epithelial cell growth until the inner portion 104 is biodegraded.

In one embodiment, the stent 100 includes a middle portion 110 that includes drugs that prevent an infiltration of cells. The middle portion 110 includes drugs enclosed within voids 105 that inhibit the growth of undesirable infiltrating cells. The drugs may also be included within the collagen/laminin matrix 101 or the polylactic acid.

The stent 100 also includes an outer portion 112 that includes antithrombogenic drugs. The antithrombogenic drugs are also included within voids 105 of the matrix 101. The antithrombic drugs may also be included within the collagen/laminin matrix 101 or the polylactic acid. The outer portion 112 includes an outer surface 114 that faces a fluid flow passing through the lumen of the vessel.

Figure 8:
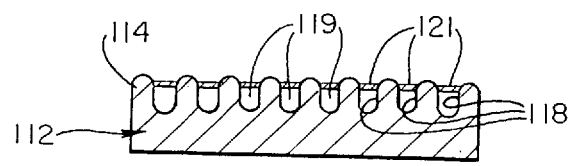
FIG. 8 is an enlarged cross-sectional view of an outer surface of one embodiment of the biodegradable coiled stent of the present invention.

In one embodiment, the outer surface 114 is irregular and delineates pores 118, such as are illustrated in FIG. 8. The irregular outer surface 114 is a consequence of the conformation of the quasi-crystalline structure of the matrix 101 used to make the outer portion 112. In one embodiment, the pores 118 are filled with a gel 119, made of collagen, such as is illustrated in FIG. 8.

The outer portion 112 most preferably includes an anticoagulant, included within voids 105. In one embodiment, the gel 119 is impregnated with the anti-coagulant. The formulation of the gel 119 and anti-coagulant is preferably very slowly dissolving. The rate of dissolution may be further slowed by a hydrolysis reaction that occurs between the gel 119 and blood. The hydrolyzed gel provides a dissolution barrier 121 that dampens the rate of dissolution of the underlying gel 119.

Two components of the matrix 101, the collagen IV and the polylactic acid, are hydrophobic and hydrophilic, respectively. Consequently, in one embodiment the collagen IV matrix is cast separately from the polylactic acid. In one preferred manufacturing embodiment, a matrix of collagen IV/laminin/gag is cast and is permitted to thoroughly dry. The matrix may then be plasma treated to improve the matrix receptivity to the polylactic acid polymer. Once the matrix has dried, a solution of polylactic acid is cast onto the matrix. Once dried, the stent 100 is cut from the matrix and is coiled.

To make a tube embodiment, the collagen may be coated on a mandrel, dried, and dipped into a polymer solution. In one other embodiment, the polylactic acid is particulated and is dispersed within the matrix of collagen IV/laminin and gag.

The stent 100 is installed in the lumen of a vessel by methods previously described for the coiled stent 50. In one embodiment, the polylactic acid includes microcapsules containing a crosslinking agent that is released when the microcapsules are ruptured. The microcapsules are ruptured in situ, once the stent 100 is positioned at a desired site in a lumen.

One advantage of using the variety of biodegradable materials within the tubular main body embodiment of FIG. 1 the coiled stent embodiment 50 of FIG. 4, and the matrix stent 100 is control of degradation. Biodegradable materials degrade at different rates, ranging from weeks to several years. Consequently, the presence of different biodegradable materials in the stent permits the stent to degrade in a predictable, orchestrated fashion.

The stent embodiments of the present invention further include incorporation of a drug or drugs or other biologically active materials. The drugs are contained within the biodegradable materials of which the stent is composed. As the stent biodegrades, drugs are administered to the surrounding tissue or to the blood stream. Thus, the rate of drug release is controlled by the rate of degradation of the biodegradable materials. A material that degrades rapidly will release the drug faster than a material that degrades slowly.

Additionally, the rate of drug release can either accelerate or slow down the rate of degradation of the biodegradable material. Thus, the rate of release of a drug acts as a control quantity for the rate of degradation. For instance, one coiled stent embodiment could include a coiled main body made from a strip having four layers. A first layer, contacting the vessel wall, could incorporate the drug, fibronectin. A second layer contacting the first layer, could incorporate the drug fibronectin at a lower concentration than the first layer. A third layer contacting the second layer could incorporate fibronectin at a lower concentration than either the first or the second layer. A fourth layer could contact the fluid passing through the lumen and could incorporate the drug, heparin.

The drug fibronectin accelerates growth of cells surrounding the stent. The accelerated growth of cells accelerates resorption reactions of the first layer of the stent. A reduced fibronectin concentration in the second and third layers slows down the resorption reactions so that the degradation of the first three layers will proceed at a cumulative rate that is compatible with the degradation of the fourth layer.

Drugs are incorporated into the biodegradable stent using techniques known in the art. The techniques include simple mixing or solubilizing with polymer solutions, dispersing into the biodegradable polymer during the extrusion of melt spinning process, or coating onto an already formed film or fiber. In one embodiment, hollow fibers, which contain anti-thrombogenic drugs, are arranged in a parallel concentric configuration with solid fibers for added support for use on the outer surface 16 of the main body 11 of the stent 10.

Further, drugs can be incorporated into the film of both the inner and outer surfaces by using methods such as melting or solvation. If an interior film layer is present within the main body as well, the interior layer and inner and outer surfaces are then combined with each other such as by mechanically pressing one layer to the other layer in a process augmented by heat or solvation adhesives. In another embodiment, drugs or biologically active agents are incorporated into the film layer and surfaces by entrapment between the layers and surfaces of biodegradable material sandwiched together, thereby further promoting release of the drugs or agents at different rates.

The drugs or other biologically active materials incorporated into the stent of the present invention perform a variety of functions. The functions include but are not limited to an anti-clotting or anti-platelet function; and preventing smooth muscle cell growth on the inner surface wall of the vessel. The drugs include but are not limited to drugs that inhibit or control the formation of thrombus or thrombolytics such as heparin or heparin fragments, aspirin, coumadin, tissue plasminogen activator (TPA), urokinase, hirudin, and streptokinase, antiproliferatives (methotrexate, cisplatin, fluorouracil, Adriamycin, and the like) antioxidants (ascorbic acid, carotene, B, vitamin E, and the like), antimetabolites, thromboxane inhibitors, non-steroidal and steroidal anti-inflammatory drugs, Beta and Calcium channel blockers, genetic materials including DNA and RNA fragments, and complete expression genes, carbohydrates, and proteins including but not limited to antibodies (monoclonal and polyclonal) lymphokines and growth factors, prostaglandins, and leukotrienes. The stent also incorporates bioactive materials such, as fibronectin, laminin, elastin, collagen, and intergrins. Fibronectin promotes adherence of the stent to the tissue of the vessel 12.

In one specific example of a biodegradable material incorporating drugs, a poly-L-lactide having an intrinsic viscosity of 2.3 dl/g is used to form monofilament fibers using a spin or melt spinning process. Five percent aspirin or 5% heparin was incorporated into the melt of the poly-L-lactide prior to fiber formation. The fibers formed had a diameter of approximately 0.5 millimeters. The monofilaments were then stretched under temperatures ranging from 50° C. to 200° C. to orient the fiber. The temperature employed depends upon the kind of material used to make the fiber. The final diameter of the oriented fiber falls within a range of 0.1 to 0.3 millimeters. Similar processing was used to incorporate 5% aspirin or 5% heparin into poly-L-lactide and polyglycolide.

Just as the use of a variety of biodegradable materials facilitates a controlled degradation of the biodegradable stent, so similarly does the incorporation of a variety of drugs into the biodegradable materials facilitate control of drug release to perform a variety of functions. For instance, drugs released from the outer surface as the outer surface degrades facilitate adherence of the stent to the inner surface wall 24 of the vessel 12. Drugs released from fibers perform a variety of functions, ranging from promoting cell growth to altering the blood clotting mechanisms, depending upon from what fiber the drug is released. In one embodiment, drugs released from the inner surface 22 of the stent as the inner surface degrades temper platelet function in blood flowing through the lumen 13.

The rate of release of drugs promoting cell growth has the capability of increasing the rate of degradation of the biodegradable stent by increasing a rate of resorption. Similarly, the rate of release of drugs promoting cell growth has the capability of decreasing the rate of degradation by decreasing the rate of resorption. The stent of the present invention, includes embodiments where drugs are incorporated in a manner that both increases and decreases the rate of degradation of the biodegradable stent over the life of the stent.

Although the present invention has been described with reference to preferred embodiments, workers skilled in the art will recognize that changes may be made in form and detail without departing from the spirit and scope of the invention.

What is claimed is:

1. A stent having a generally tubular main body for insertion into a lumen of a vessel of a living being wherein the tubular main body comprises a substantially biodegradable matrix that includes collagen IV and laminin that enclose voids within the matrix, and a biodegradable strengthening material composed of polylactic acid in contact with the matrix to strengthen the matrix, the tubular main body being essentially saturated with drugs and said tubular main body being expandable within a lumen of a vessel of a living being.

2. The stent of claim 1 wherein the strengthening material includes particles dispersed within the biodegradable matrix.

3. The stent of claim 1 wherein the strengthening material includes a layer attached to the matrix.

4. The stent of claim 1 wherein the biodegradable matrix further includes a glycosaminoglucuronan.

5. The stent of claim 4 wherein the glycosaminoglucuronan includes heparin.

6. A stent having a generally tubular main body for insertion into a lumen of a vessel of a living being wherein the tubular main body comprises a substantially biodegradable matrix that includes collagen IV and laminin that enclose voids within the matrix, and a biodegradable strengthening material in contact with the matrix to strengthen the matrix, the tubular main body being essentially saturated with drugs, wherein the drugs include microencapsulated drugs.

* * * * *

UNITED STATES PATENT AND TRADEMARK OFFICE
CERTIFICATE OF CORRECTION

PATENT NO. : 5,769,883

DATED : June 23, 1998

INVENTOR(S) : Paul Buscemi et al

It is certified that error appears in the above-identified patent and that said Letters Patent is hereby corrected as shown below:

Col. 1, line 37, delete "4,768,5107" and insert -- 4,768,507 --;

Col. 6, line 20, delete "arid" and insert -- and --.

Signed and Sealed this

Nineteenth Day of January, 1999

Attest:

Attesting Officer

*Acting Commissioner of Patents and Trademarks*